US008107082B1

(12) United States Patent
Kim et al.

(10) Patent No.: US 8,107,082 B1
(45) Date of Patent: Jan. 31, 2012

(54) SPR APPARATUS WITH A HIGH PERFORMANCE FLUID DELIVERY SYSTEM (75) Inventors: Gilbum Kim, Placentia, CA (US); Hannwen Guan, Bothwell, WA (US); Shuxin Cong, Bellevue, WA (US)

(73) Assignee: Plexera LLC, Woodinville, WA (US)

( * ) Notice: Subject to any disclaimer, the term of this patent is extended or adjusted under 35 U.S.C. 154(b) by 0 days.

(21) Appl. No.: 13/187,510

(22) Filed: Jul. 21, 2011

Related U.S. Application Data (62) Division of application No. 12/339,017, filed on Dec. 18, 2008, now Pat. No. 8,004,669.

(60) Provisional application No. 61/008,263, filed on Dec. 18, 2007.

(51) Int. Cl.
G01N 21/00 (2006.01)
(52) U.S. Cl. ........................................ 356/445; 356/244
(58) Field of Classification Search .......... 356/445–448, 356/244–246
See application file for complete search history.

(56) References Cited

U.S. PATENT DOCUMENTS

| 3,105,902 A | 10/1963 | Ostrofsky |
| 3,751,587 A | 8/1973 | Insler |
| 3,891,507 A | 6/1975 | Breuer |
| 3,990,850 A | 11/1976 | Friedman |
| 4,038,030 A | 7/1977 | Albright |
| 4,148,057 A | 4/1979 | Jesse |
| 4,375,025 A | 2/1983 | Carlson |
| 4,585,931 A | 4/1986 | Duncan |
| 4,638,144 A | 1/1987 | Latta |
| 4,707,722 A | 11/1987 | Folk |
| 4,719,502 A | 1/1988 | Ikeya |
| 4,753,863 A | 6/1988 | Spanjer |
| 4,789,804 A | 12/1988 | Karube |
| 4,861,620 A | 8/1989 | Azuma |
| 4,945,045 A | 7/1990 | Forrest |
| 4,945,204 A | 7/1990 | Nakamura |
| 4,997,278 A | 3/1991 | Finlan |
| 5,030,551 A | 7/1991 | Herren |
| 5,068,124 A | 11/1991 | Batey |
| 5,078,855 A | 1/1992 | Mochizuki |
| 5,089,112 A | 2/1992 | Skotheim |
| 5,104,619 A | 4/1992 | de Castro |
| 5,116,481 A | 5/1992 | Ozawa |
| 5,157,412 A | 10/1992 | Kleinschmidt |
| 5,192,507 A | 3/1993 | Taylor |

(Continued)

FOREIGN PATENT DOCUMENTS

DE  10064146  12/2000

(Continued)

OTHER PUBLICATIONS

Brockman et al., "Surface Plasmon Resonance Imaging Measurements of Ultrathin Organic Films", Ann. Rev. Phys. Chem., 2000, 51:41-63.

(Continued)

*Primary Examiner* — Michael P Stafira
(74) *Attorney, Agent, or Firm* — Sci-Law Strategies, PC (57) ABSTRACT

An apparatus may include a flow cell for a surface plasmon resonance test apparatus and a fluid delivery system operatively coupled to the flow cell and configured to deliver a plurality of fluids to the flow cell substantially continuously. The fluid delivery system may include two pumps for pumping the fluids.

19 Claims, 6 Drawing Sheets

U.S. PATENT DOCUMENTS

| | | |
|---|---|---|
| 5,200,051 A | 4/1993 | Cozzette |
| 5,206,280 A | 4/1993 | Williams |
| 5,242,828 A | 9/1993 | Bergstrom |
| 5,246,846 A | 9/1993 | Pittner |
| 5,262,470 A | 11/1993 | Shimotsuma |
| 5,268,305 A | 12/1993 | Ribi |
| 5,313,264 A | 5/1994 | Ivarsson |
| 5,329,090 A | 7/1994 | Woelki |
| 5,346,802 A | 9/1994 | Ohbachi |
| 5,357,077 A | 10/1994 | Tsuruta |
| 5,368,712 A | 11/1994 | Tomich |
| 5,373,039 A | 12/1994 | Sakai |
| 5,401,378 A | 3/1995 | King |
| 5,405,783 A | 4/1995 | Pirrung |
| 5,413,629 A | 5/1995 | Yasui |
| 5,415,838 A | 5/1995 | Rieger |
| 5,436,161 A | 7/1995 | Bergstrom |
| 5,436,170 A | 7/1995 | Cornell |
| 5,445,923 A | 8/1995 | Takahashi |
| 5,474,796 A | 12/1995 | Brennan |
| 5,478,756 A | 12/1995 | Gizeli |
| 5,485,277 A | 1/1996 | Foster |
| 5,491,097 A | 2/1996 | Ribi |
| 5,492,840 A | 2/1996 | Malmqvist |
| 5,512,131 A | 4/1996 | Kumar |
| 5,514,501 A | 5/1996 | Tarlov |
| 5,527,711 A | 6/1996 | Tom-Moy |
| 5,536,822 A | 7/1996 | Haystead |
| 5,567,301 A | 10/1996 | Stetter |
| 5,571,568 A | 11/1996 | Ribi |
| 5,580,794 A | 12/1996 | Allen |
| 5,622,872 A | 4/1997 | Ribi |
| 5,624,537 A | 4/1997 | Turner |
| 5,629,790 A | 5/1997 | Neukermans |
| 5,637,201 A | 6/1997 | Raguse |
| 5,688,642 A | 11/1997 | Chrisey |
| 5,693,477 A | 12/1997 | Cornell |
| 5,707,502 A | 1/1998 | McCaffrey |
| 5,716,778 A | 2/1998 | Weng |
| 5,719,060 A | 2/1998 | Hutchens |
| 5,723,345 A | 3/1998 | Yamauchi |
| 5,736,410 A | 4/1998 | Zarling |
| 5,741,409 A | 4/1998 | Raguse |
| 5,753,093 A | 5/1998 | Raguse |
| 5,756,355 A | 5/1998 | Lang |
| 5,783,054 A | 7/1998 | Raguse |
| 5,798,030 A | 8/1998 | Raguse |
| 5,824,483 A | 10/1998 | Housten |
| 5,834,224 A | 11/1998 | Ruger |
| 5,844,099 A | 12/1998 | Stahl |
| 5,846,842 A | 12/1998 | Herron |
| 5,922,594 A | 7/1999 | Lof |
| 5,922,617 A | 7/1999 | Wang |
| 5,938,595 A | 8/1999 | Glass |
| 5,942,388 A | 8/1999 | Willner |
| 5,955,379 A | 9/1999 | Lennox |
| 5,985,377 A | 11/1999 | Corbet |
| 6,020,208 A | 2/2000 | Hutchens |
| 6,027,942 A | 2/2000 | Hutchens |
| 6,074,616 A | 6/2000 | Buechler |
| 6,096,825 A | 8/2000 | Garnier |
| 6,101,946 A | 8/2000 | Martinsky |
| 6,113,992 A | 9/2000 | Corbet |
| 6,146,593 A | 11/2000 | Pinkel |
| 6,197,599 B1 | 3/2001 | Chin |
| 6,217,949 B1 | 4/2001 | Corbet |
| 6,218,194 B1 | 4/2001 | Lyndin |
| 6,219,138 B1 | 4/2001 | Swanson |
| 6,225,047 B1 | 5/2001 | Hutchens |
| 6,232,066 B1 | 5/2001 | Felder |
| 6,245,590 B1 | 6/2001 | Wine |
| 6,291,155 B1 | 9/2001 | Raguse |
| 6,322,970 B1 | 11/2001 | Little |
| 6,329,209 B1 | 12/2001 | Wagner |
| 6,340,597 B1 | 1/2002 | Svorc |
| 6,362,912 B1 | 3/2002 | Lewis |
| 6,379,929 B1 | 4/2002 | Burns |
| 6,380,365 B1 | 4/2002 | Akerstrom |
| 6,406,921 B1 | 6/2002 | Wagner |
| 6,421,164 B2 | 7/2002 | Tearney |
| 6,433,907 B1 | 8/2002 | Lippert |
| 6,447,723 B1 | 9/2002 | Schermer |
| 6,448,065 B2 | 9/2002 | Laugharn |
| 6,448,089 B1 | 9/2002 | Vuong |
| 6,472,179 B2 | 10/2002 | Stahl |
| 6,482,593 B2 | 11/2002 | Walt |
| 6,485,918 B1 | 11/2002 | Schermer |
| 6,489,106 B1 | 12/2002 | Shivashankar |
| 6,545,758 B1 | 4/2003 | Sandstrom |
| 6,548,171 B1 | 4/2003 | Barbera-Guillem |
| 6,558,623 B1 | 5/2003 | Ganz |
| 6,565,813 B1 | 5/2003 | Garyantes |
| 6,569,385 B1 | 5/2003 | Little |
| 6,586,193 B2 | 7/2003 | Yguerabide |
| 6,785,433 B2 | 8/2004 | Tiefenthaler |
| 6,787,368 B1 | 9/2004 | Wong |
| 6,870,627 B2 | 3/2005 | Elkind |
| 6,902,705 B1 | 6/2005 | Caillat |
| 6,911,344 B1 | 6/2005 | Reichert |
| 6,980,294 B2 | 12/2005 | Namba |
| 7,041,208 B2 | 5/2006 | Staats |
| 7,081,954 B2 | 7/2006 | Sandstrom |
| 7,126,688 B2 | 10/2006 | Rassman |
| 7,244,396 B2 * | 7/2007 | Chait et al. .................... 422/501 |
| 7,312,069 B2 | 12/2007 | Ban |
| 7,319,046 B2 | 1/2008 | Misiakos |
| 7,417,726 B2 * | 8/2008 | Kao et al. .................... 356/243.1 |
| 7,429,479 B2 * | 9/2008 | Harding .................... 435/288.4 |
| 7,463,358 B2 | 12/2008 | Wolf |
| 7,695,976 B2 | 4/2010 | Kim |
| 7,745,143 B2 | 6/2010 | Casasanta, III |
| 7,889,347 B2 | 2/2011 | Guan |
| 8,004,669 B1 | 8/2011 | Kim |
| 2002/0024495 A1 | 2/2002 | Lippert |
| 2002/0044893 A1 | 4/2002 | Corn |
| 2002/0068813 A1 | 6/2002 | Dragic |
| 2002/0127565 A1 | 9/2002 | Cunningham |
| 2002/0140938 A1 | 10/2002 | Naya |
| 2002/0197729 A1 | 12/2002 | Tsuzuki |
| 2003/0082820 A1 | 5/2003 | Perbost |
| 2003/0107741 A1 | 6/2003 | Pyo |
| 2004/0008345 A1 | 1/2004 | Nurmikko |
| 2004/0014946 A1 | 1/2004 | Chao |
| 2004/0048311 A1 | 3/2004 | Ault-Riche |
| 2004/0067597 A1 | 4/2004 | Datwani |
| 2004/0174518 A1 | 9/2004 | Naiki |
| 2004/0214233 A1 | 10/2004 | Lubman |
| 2004/0248144 A1 | 12/2004 | Mir |
| 2005/0002085 A1 | 1/2005 | Matsui |
| 2005/0046848 A1 | 3/2005 | Cromwell |
| 2005/0095577 A1 | 5/2005 | Yang |
| 2006/0091051 A1 | 5/2006 | Takada |
| 2006/0154320 A1 | 7/2006 | Zuk |
| 2006/0187459 A1 | 8/2006 | Ok |
| 2006/0234265 A1 | 10/2006 | Richey |
| 2007/0009198 A1 | 1/2007 | Petcavich |
| 2007/0059817 A1 | 3/2007 | Aoyagi |
| 2007/0081163 A1 | 4/2007 | Liang |
| 2007/0099180 A1 | 5/2007 | Robotti |
| 2007/0122314 A1 | 5/2007 | Strand |
| 2007/0128455 A1 | 6/2007 | Wolf |
| 2007/0140918 A1 | 6/2007 | Yin |

FOREIGN PATENT DOCUMENTS

| | | |
|---|---|---|
| WO | WO 93/15110 | 8/1993 |
| WO | WO 95/31480 | 11/1995 |
| WO | WO 96/02830 | 2/1996 |
| WO | WO 96/09547 | 3/1996 |
| WO | WO 97/07593 | 1/1997 |
| WO | WO 97/41424 | 1/1997 |
| WO | WO 97/41425 | 1/1997 |
| WO | WO 97/12988 | 4/1997 |
| WO | WO 02/052260 | 7/2002 |

OTHER PUBLICATIONS

Bogoyevitch et al., "Peptide inhibitors of protein kinases-discovery, characterisation and use", Biochim. Biophys. Acta, 2005, 1754: 79-99.

Davies et al., "Polymer Membranes in clinical sensor applications III. Hydrogels as reactive matrix membranes in fiber optic sensors", Biomaterials, 1992 13:991-999.

Dzgoev et al., "Microformat Imaging ELISA for Pesticide Determination" 1996, Anal Chem. 68:3364-3369.

Hines et al., "Bisubstrate analog probes for the insulin receptor protein kinase: Molecular yardsticks for analyzing catalytic mechanism and inhibitor design", Bioorg. Chem., 2005, 33:285-297.

Hu, J.C., et al., "Sequence Requirements for Coiled-Coils: Analysis with .lambda. Repressor-GCN4 Leucine Zipper Fusions" Science 250:1400-1403 (1990).

Hyun et al., "Enzymatic Nanolithography of a self assembled Oligionucleotide Monolayer on Gold", *J. Am Chem. Soc.*, 2004, 126:4770-4771.

Komatsu, et al., "SPR sensor signal amplification based on dye-doped polymer particles" Sci Tech. Adv. Mater., 2006 7:150-155.

Krasnoslobodtsev et al., Langmuir 18:3181-3184 (2002).

Mitchell et al., "Sensitivity enhancement of surface plasmon resonance biosensing of small molecules" Anal Biochem, 2005, 343:125-135.

P. Anton van der Merwe, "Surface Plasmon Resonance", May 27, 2005, http://web.archive.org/web/20050527002318/http://users.path.ox.ac.uk/-vdmerwe/internal/spr.PDF.

Qi et al., "Determination of the Bioavailability of Biotin Conjugated onto Shell Cross-Linked (SCK) Nanoparticles", J. Am. Chem. Soc., 2004 126:6599-6607.

Ramachandran et al., "Self-assembling protein microarrays", Science, 2004, 305:86-90.

Severs and Schasfoort, "Enhanced Surface Plasmon Resonance Inhibition Test (ESPRIT) using latex particles", Biosens. Bioelectron., 1993, 8:365-370.

Shen et al., "Protein kinase structure and function analysis with chemical tools" Biochim. Biophys. Acta, 2005, 1754:65-78.

Wagner et al., "Bioreactive Self-assembled Monolayers on Hydrogen-Passivated Si(111) as a new class of atomically flat substrates for Biological Scanning Probe Microscopy", 1997, J. Structural Biol., 119:189-201.

Wink et al., "Liposome-Mediated Enhancement of the Sensitivity in Immunoassays of Proteins and Peptides in Surface Plasmon Resonance Spectrometry" Anal. Chem., 1998, 70:827-832.

Xia et al., "Surface Patterning and its Application in Wetting/Dewetting Studies" Current Opinion in Colloid & Interface Science, 2001 6:54-64.

Zhong et al., "Soft Lithographic Approach to the Fabrication of Highly Ordered 2D Arrays of Magnetic Nanoparticles on the Surfaces of Silicon Substrates", Langmuir, 2000 16:10369-10375.

International Search Report dated Jul. 3, 2008, Application No. PCT/US06/44957.

International Search Report dated May 10, 2007, Application No. PCT/US06/22123.

International Search Report dated Nov. 10, 2008, Application No. PCT/US08/74865.

Dudek et al.; U.S. Appl. No. 12/061,175, filed Apr. 2, 2008.

Schwoerer et al.; U.S. Appl. No. 12/392,893, filed Feb. 25, 2009.

\* cited by examiner

SPR APPARATUS WITH A HIGH PERFORMANCE FLUID DELIVERY SYSTEM

PRIORITY CLAIM

This application is a divisional of and claims priority to (1) U.S. Utility application Ser. No. 12/339,017 entitled "SPR APPARATUS WITH A HIGH PERFORMANCE FLUID DELIVERY SYSTEM", inventors: Gilbum Kim et al., filed on Dec. 18, 2008 which issued as U.S. Pat. No. 8,004,669 and (2) U.S. Provisional Application No. 61/008,263, filed Dec. 18, 2007, entitled "SPR APPARATUS WITH A HIGH PERFORMANCE FLUID DELIVERY SYSTEM", inventors: Gibum Kim et al. These applications (1)-(2) are herein expressly incorporated by reference in their entireties.

BACKGROUND OF THE INVENTION

Surface Plasmon Resonance (SPR) may be used to investigate the binding characteristics of chemical and/or biochemical entities such as molecules or biomolecules found (or potentially found) in an analyte to a microarray of test patches. It may be desirable to expose the microarray to a series of analytes, buffers, washes, etc. to perform one or more tests using a flow cell. In some embodiments, it may be necessary to provide flow to an SPR flow cell for several hours or more, such as to accurately determine low value kinetic constants, to perform a series of tests over a period of time, etc.

Since SPR effectively measures local indices of refraction at the test patches on the microarray surface, and changes in fluid pressure or flow may affect the index of refraction, it may be desirable to minimize variations in fluid pressure within the test cell. It may also be desirable to minimize periods of non-flow through the flow cell, such as to maximize throughput, preserve concentration gradients near test patches, maintain fluid temperature, maximize reactivity of the test patches, allow for complex test protocols, collect data for accurate determination of kinetic constants, and/or provide other benefits.

OVERVIEW

According to an embodiment, an SPR test apparatus includes a fluid delivery system operable to provide a substantially continuous flow of fluids to an SPR microarray flow cell.

According to another embodiment, an SPR fluid delivery system includes a plurality of pumps operable to pump fluids through the flow cell.

According to another embodiment, an SPR fluid delivery system is operable to maintain flow through a flow cell even during a loading step when an analyte is withdrawn from an analyte source into a holding coil.

According to another embodiment, an SPR fluid delivery system includes an injection valve operable to substantially maintain flow through a flow cell from a plurality of pumps.

According to another embodiment, an SPR fluid delivery system is configured to switch fluids flowing through portions of the fluid delivery system while preventing the flow of at least one of the fluids through a fluid delivery pump.

According to another embodiment, an SPR test apparatus is configured to expose a flow cell to a series of different fluids with only switching delays in the fluid flow.

DETAILED DESCRIPTION

In the following detailed description, reference is made to the accompanying drawings, which form a part hereof. In the drawings, similar symbols typically identify similar components, unless context dictates otherwise. Other embodiments may be used and/or and other changes may be made without departing from the spirit or scope of the disclosure.

Figure 1:
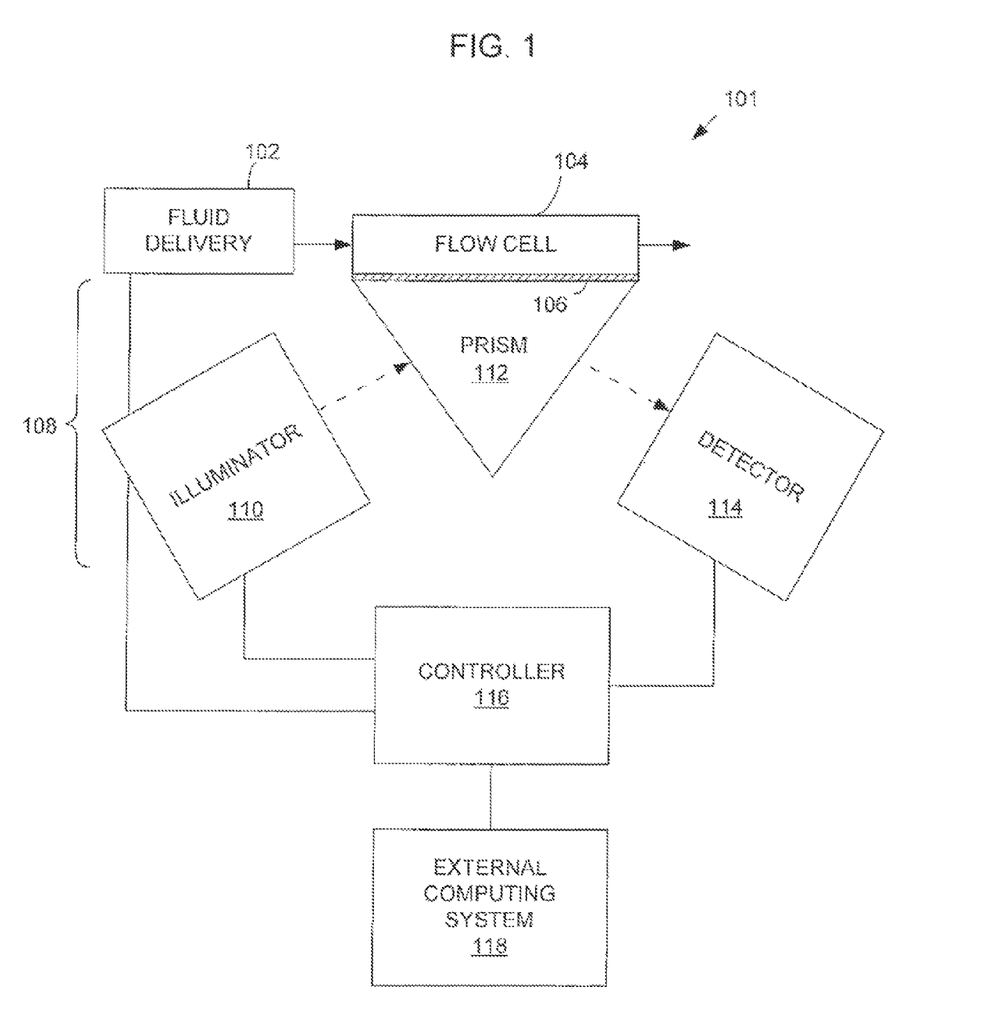
FIG. 1 is a diagram of an SPR test system, according to an embodiment.

FIG. 1 is a diagram of an SPR test system 101, according to an embodiment. The fluid delivery system 102 includes a complex of flow channels, valves, pumps, and/or other components configured to provide a substantially constant flow of fluid from a plurality of fluid sources to a flow cell 104. According to embodiments, the flow cell 104 may be operatively coupled to a microarray 106 having an SPR coupling surface. The microarray 106 may be constructed as a half volume configured to maintain an electrooptical relationship between the SPR coupling surface and a planar array of test patches (not shown). The microarray includes areas of specific affinity for one or more particular polypeptides, proteins, polynucleotides, kinases, and/or other small molecules. The areas of specific affinity may be referred to as test patches or regions of interest (ROI). The test patches may generally be separated by one or more continuous areas resistant to non-specific binding of one or more of the above.

The test patches include binding moieties such as anchored proteins that extend upward from the surface of the microarray into the fluid in and flowing through the flow cell 104. If an analyte flowing through the flow cell includes a particular molecule or biomolecule for which the binding moiety of a particular test patch has affinity, the molecule or biomolecule may bind to or associate with the binding moiety according to a characteristic association kinetic. Association of the molecule or biomolecule to the test patch changes the index of refraction in a volume near the test patch.

If another analyte or buffer solution is then flowed across the microarray, and the other analyte or buffer solution does not include the particular molecule or biomolecule, the bound molecule or biomolecule may dissociate from the binding moiety of the test patch according to a characteristic dissociation kinetic. Dissociation of the molecule or biomolecule from the test patch again changes the index of refraction of the volume near the test patch. Generally, complete dissociation may reduce the index of refraction to near the starting index of refraction before the initial binding. However, complete dissociation may take a very long time and/or the index of refraction may not quite return to its original value. Moreover, a series of associations and dissociations may result in a gradual change in the index of refraction.

As will be discussed below, the microarray and the test patch may be regenerated by flowing a wash fluid, such as water, a detergent, and/or an acid for example, through the flow cell. Such regeneration may generally return the index of refraction near the test patch to near its original value.

An optical interface assembly 108 is operable to illuminate the SPR coupling surface and detect variations in the amount of reflected light energy. The amount of reflected light energy is, in turn, affected by binding (or not) of a molecule or biomolecule from an analyte onto the test patches.

The optical interface assembly typically includes an illuminator 110 configured to illuminate the SPR coupling surface. The illuminator 110 may include a number of discrete and/or integrated components operative to produce the illumination. Typically, a coupling assembly such as a prism 112 is aligned to receive light from the illuminator 110 and couple it to the SPR coupling surface. A portion of the photons of light may be converted to surface plasmons. The remaining photons are reflected from the SPR coupling surface, and the coupling assembly 112 is configured to couple them out to a detector 114. The detector is operable to detect variations in the proportion of photons reflected from across the surface of the SPR coupling surface, the variations typically including a component related to the association and dissociation of molecular and/or biomolecular moieties from the analyte onto one or more of the test patches. Typically, higher loading (i.e., a greater proportion of binding moiety active sites being associated with the specific molecule or biomolecule) tends to increase the conversion of photons to surface plasmons (and hence reduce the number of reflected photons), and lower loading tends to minimize the conversion of photons to surface plasmons (and hence maximize the number of reflected photons).

A controller 116 may be operatively coupled to the fluid delivery system 102, the illuminator 110, and/or the detector 114, and may include an interface to an external computing system or network 118. Alternatively, the interface to the external computing system or network 118 may be omitted and the apparatus 101 may operate as a stand-alone system. The controller may be used to control the output of the illuminator 110, perform image processing on the image acquired by the detector 114 or transmit image data to an external processor 118 for image processing, perform data analysis or transmit image data to an external processor 118 for data analysis, transmit and receive status and command data to and from internal components and external systems, provide a human interface via a keyboard, display, and/or other status indicators (not shown), and control the fluid delivery system 102. In particular, the fluid delivery system may include pumps and valves with electrical control interfaces, and the controller 116 may transmit signals to operate the pumps, valves, etc. of the fluid delivery system 102.

The microarray 106 may include a relatively large number of test patches (ROIs), each having specificity for associating a particular molecule or biomolecule. According to an embodiment, a system described herein included well over 1000 test patches and was designed to accommodate about 5000 test patches. The test patches may all have different specificities, or a given association specificity may be repeated across a number of test patches.

SPR systems with a large microarray 106, i.e. a microarray with a large number of test patches, may have a particularly high sensitivity to variations in fluid flow through the flow cell. One reason for this is that, for a detector 114 including an image plane detector such as a CCD or CMOS array, a large array of test patches may reduce the number of pixels corresponding to each test patch. Reducing the number of pixels may tend to decrease averaging and increase susceptibility to shot and/or electronic noise. This may account for a relatively large proportion of the noise budget in the system. Variations in fluid pressure may further increase system noise, which may decrease accuracy and/or precision.

Figure 2:
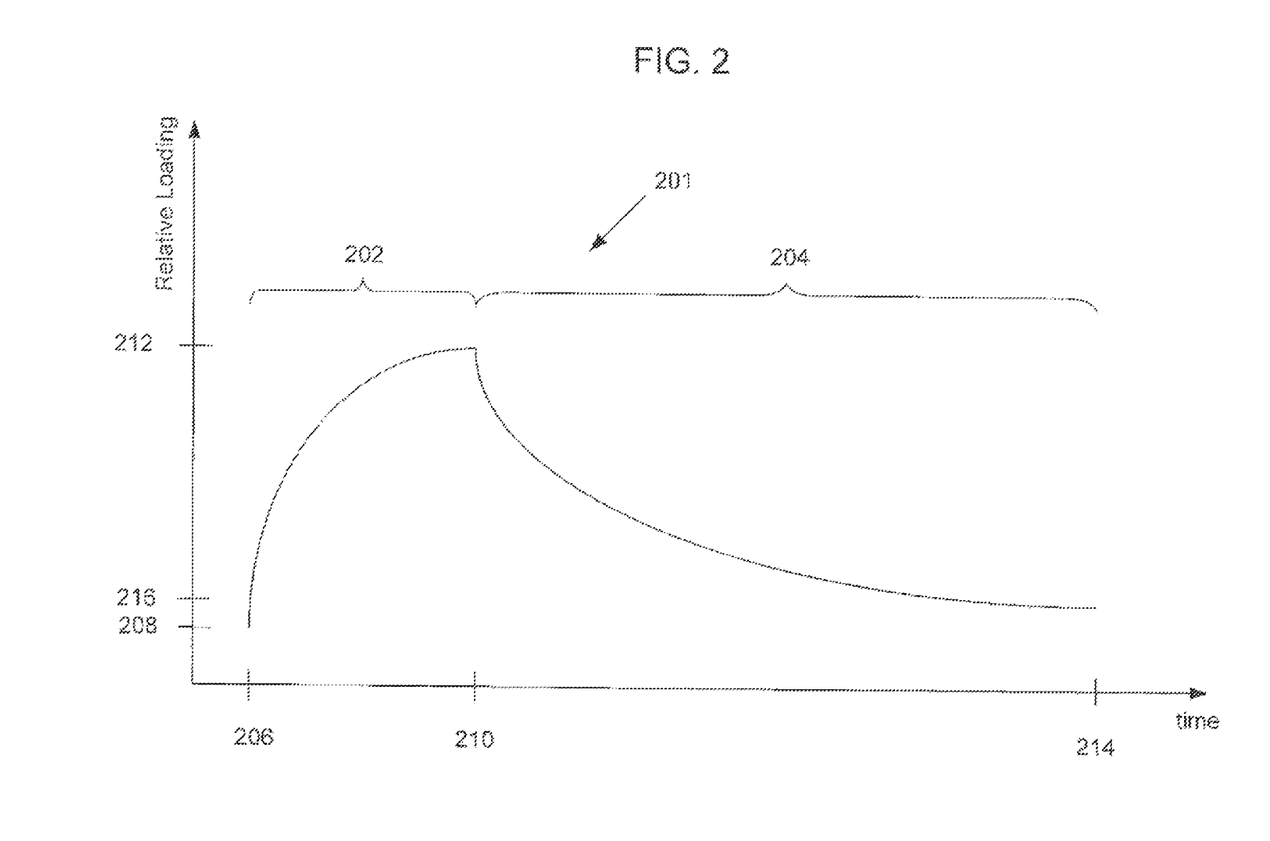
FIG. 2 is a chart showing idealized association and dissociation curves of a molecule or biomolecule from an analyte onto a test patch on a microarray, according to an embodiment.

FIG. 2 is a chart showing idealized association and dissociation curves 201 of a molecule or biomolecule from an analyte onto a test patch, according to an embodiment. The horizontal axis represents time and the vertical axis represents relative loading. Relative loading may correspond to the surface concentration of the molecule or biomolecule associated with the test patch. In the example of FIG. 2, it is assumed that the molecule or biomolecule is a substance that has affinity for the test patch represented.

The curve 201 includes an association curve 202 that is generated or derived from a corresponding association phase 202. A dissociation curve 204 is generated or derived from a corresponding dissociation phase 204. At an initial time 206, a test patch on the microarray surface may exhibit relative loading 208, which in turn may be exhibited as a minimum attenuation of reflected energy detected by the detector 114 of FIG. 1. In many cases, loading 208 may correspond to substantially zero loading—e.g. no molecules or biomolecules being bound to the test patch.

At time 206, an analyte containing the molecule or biomolecule is injected into the flow cell. During the association phase 202, progressively greater amounts of the molecule or biomolecule bind to, or associate with the test patch as the analyte containing the molecule or biomolecule flows across the surface of the test patch. The shape of the association curve 202 may be used to determine the kinetic constant for association ka and other aspects of the association kinetics (e.g. whether the kinetics are first order). At some loading 212, the association phase of the experiment may end coincident with a time 210. Typically, association kinetics may be relatively fast and the association phase 202 may last only several minutes.

At time 206, the flow of the analyte containing the molecule or biomolecule is stopped, and a different fluid is injected through the flow cell as the dissociation phase 204 begins. According to embodiments, the different fluid may include a buffer solution. To minimize effects of quiescent fluid holding chemical and/or biochemical moieties near the surface of the patch or an extended period, it may be desirable to minimize the time lag between ending flow of the analyte and beginning flow of the buffer solution. According to an embodiment, the high performance fluid delivery system 102 may be configured to switch the flow of fluids substantially instantaneously; e.g. having only a short delay corresponding to the switching time of a valve, start-up of a pump, etc. For example, the switching delay may be on the order of 100 milliseconds or less in some embodiments. For example, the switching delay may be on the order of 10 milliseconds in other embodiments. In another example, the switching delay may be on the order of 1 millisecond in still other embodiments. According to embodiments, pressure fluctuations in the flow cell may be minimized during flow switching.

While the buffer solution flows over the surface of the test patch during the dissociation phase 204, the molecule or biomolecule may separate from, or dissociate from the test patch. Typically, the rate of dissociation may be relatively high while the surface concentration of the molecule or biomolecule is high, and then decrease as the molecule or biomolecule is successively depleted. The shape of the dissociation curve 204 may be used to determine the kinetic constant for dissociation kd and other aspects of the dissociation kinetics (e.g. whether the kinetics are first order). Taken together, the association and dissociation curves 202, 204 may be used to determine other characteristic aspects of molecule or biomolecule binding such as KA=ka/kd, equilibrium constants, etc.

At some time 214, the loading may decrease to a value 216 and the dissociation phase 204 of the experiment may end. Typically, dissociation kinetics may be relatively slower than the association phase 202, and the dissociation phase 204 may last as long as several hours. During the dissociation phase, according to an embodiment, flow of the dissociation fluid (e.g. buffer) may be kept substantially constant to avoid undesirable effects that may skew the curve 204.

In some cases, the final relatively loading 216 of the molecule or biomolecule may be different than the initial relative loading 208. When the difference in values is large enough, the microarray may need to be conditioned or regenerated to return substantially to its initial state. Regeneration may be performed during a regeneration phase (not shown). For example, during a regeneration phase, water, a detergent, an acid, or sequential combinations of water, detergent, and acid may be injected into the flow cell to remove the last tenacious bits the molecule or biomolecule that remain adhered to the test patch after conclusion of the dissociation phase 204. According to some embodiments, the regeneration phase may include correcting the chemistry of the test patch for non-specific protein binding, etc.

Figure 3:
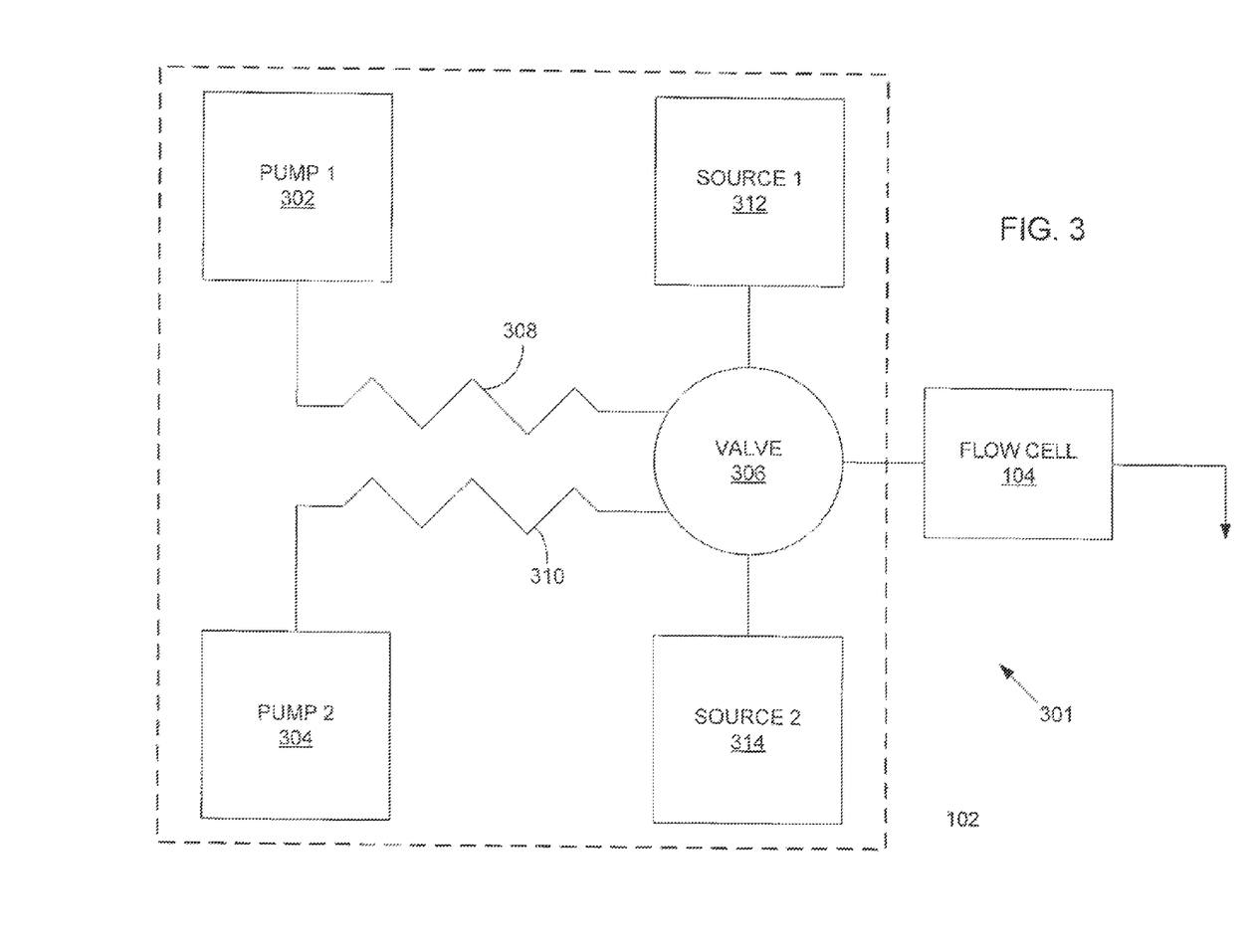
FIG. 3 is a diagram of an SPR fluid delivery system and SPR flow cell, according to an embodiment.

FIG. 3 is a diagram of a portion of an SPR test apparatus 301 including an SPR fluid delivery system 102 and a flow cell 104, according to an embodiment. The fluid delivery system 102 includes first and second pumps 302, 304 that are operatively coupled to respective ports of a valve 306. An output port of the valve 306 is operatively coupled to the flow cell 104. The first pump 302 is coupled to the valve 306 through a first holding coil 308. The second pump 304 is similarly coupled to the valve 306 through a second holding coil 310. The holding coils 308 and 310 may include extended lengths of tubing, such as relatively small diameter PTFE tubing or the like, that are configured to hold volumes of fluid from a first fluid source 312 or a second fluid source 314, which are also operatively coupled to the valve 306. For example, the first fluid source may include an analyte containing a molecule or biomolecule for test and the second fluid source may include a buffer solution.

According to an embodiment, the holding coils 308, 310 and other tubing in the fluid delivery system 201, as well as tubing connecting the fluid delivery system 201 to the flow cell 104 may include hydrophilic inner walls and/or may be coated with a hydrophilic substance such as a surfactant. Making the surfaces of the tubing hydrophilic may allow fluids such as buffers and analytes to flow more readily. This may allow reduced pump pressures and/or reduced tubing diameter. Reducing tubing diameters may help to reduce exchange volumes to allow smaller samples. Additionally, the interior surfaces of the flow cell 104 that contain the analyte contacting the microarray may be formed from or treated with a hydrophilic material. As with the holding coils 308, 310 and other tubing, such a configuration may further reduce resistance to flow, thereby further accruing the benefits described above.

Hydrophilic modification of inner surfaces may be performed, for example, by incubating plastic material in a surfactant solution such as a 10% ZONYL (Dupont) fluoroadditive in distilled water for 30 minutes. The surfactant treatment was found to be effective for a length of time greater than a single association/dissociation cycle, and in some cases long enough to complete several association/dissociation cycles.

Substantially permanent surface modification may be achieved by coating plastic surfaces with a 3-5 nanometer thickness of silica film. Alternatively, polyethylene glycol (PEG) or other hydrophilic film may be deposited by methods such as plasma enhanced chemical vapor deposition (PECVD).

In a priming phase of operation, according to an embodiment, the valve 306 is actuated to couple the first and/or second pumps 302, 304 to the second fluid source 314. The first and/or second pumps withdraw the buffer solution from the second fluid source 314 into the respective holding coils 308, 310. The coupling of the pumps 302, 304 to the second fluid source 314 may be simultaneous or sequential. Still during the priming phase, the valve 306 is actuated to couple the first and/or second pumps to the flow cell 104. The pumps simultaneously or sequentially push the buffer solution from the respective holding coils 308, 310 through the valve 306 and through the flow cell 104. During the flow, air and other impurities may be expelled from the system and into a waste receptacle (not shown).

According to an embodiment, the first pump 302 first pushes buffer from the holding coil 308 through the valve 306 and flow cell 104, and then the second pump 304 pushes buffer from the holding coil 310 through the valve 306 and the flow cell 104. When the first pump 302 is finished pumping buffer solution from the holding coil 308, the valve 306 is actuated to decouple the first pump 302 from the flow cell 104, couple the second valve 304 to the flow cell 104, and couple the first pump 302 to the first fluid source 312. While the second pump 304 pushes buffer from the holding coil 310 through the valve 306 and flow cell 104, the first pump 302 withdraws analyte from the first fluid source 312 into the first holding coil 308. When the second pump 304 is finished pumping buffer through the flow cell, the priming phase ends.

t the end of the priming phase, the association phase begins. The valve 306 is actuated to couple the first pump 302 to the flow cell 104 and the second pump 304 to the second source 314. The first pump 302 is actuated to push analyte from the holding coil 308 through the valve 306 and the flow cell 104. If a molecule or biomolecule corresponding to a test patch is present in the analyte, the moiety may progressively bind to or associate with the test patch. Progressive association may proceed in a manner corresponding to the association curve 202 shown in FIG. 2. Such binding may be detected by the optics subsystem 108 of the SPR apparatus 101 shown in FIG. 1. While the first pump 302 is pushing analyte through the valve 306 and flow cell 104, the second pump 304 is actuated to withdraw buffer solution from the second fluid source 314 into the holding coil 310. When the first pump is finished pumping analyte from the holding coil 308 through the flow cell 104, the association phase ends.

At the end of the association phase, the dissociation phase begins. The first pump 302 is stopped, the valve 306 is actuated to decouple the first pump 302 from the flow cell 104 and couple the second pump 304 to the flow cell 104, and the second pump 302 is actuated to push buffer solution from the holding coil 310 through the valve 306 and the flow cell 104. During the dissociation phase, a molecule or biomolecule associated with a test patch during the association phase may progressively dissociate from the test patch. Dissociation may follow a curve having a shape similar to the portion 204 in FIG. 2.

According to an embodiment, stopping the first pump, switching the coupling to the flow cell, and starting the second pump take place in rapid succession. According to an embodiment, the actions take place substantially simultaneously so that the flow of fluids (first the analyte and then the buffer)

through the flow cell 104 is substantially continuous. According to an embodiment, substantially continuous means about 100 milliseconds or less interruption in flow through the flow cell 104. According to another embodiment, substantially continuous means about 10 milliseconds or less interruption in flow through the flow cell 104. In still another embodiment, the flow through the flow cell 104 may be continuous to about 1 millisecond or less interruption.

While the second pump 304 is pushing buffer solution through the valve 306 and the flow cell 104, the first pump 302 may be coupled to the second fluid source 314 and withdraw buffer solution into the first holding coil 308. The first holding coil may optionally be flushed to a waste receptacle (not shown) to clean the holding coil of any remnants of the analyte from source 312. If the capacity of the second holding coil 310 is insufficient to provide flow for a period of time corresponding to the dissociation phase 204 of FIG. 2, the valve 306 and pumps 302, 304 may be switched during the dissociation phase to deliver buffer solution from the first holding coil 308. This process may be repeated in tag-team fashion until the dissociation phase is complete. As with the juncture between association and dissociation phases, pump switching during the dissociation phase may occur quickly enough to maintain substantially continuous flow of buffer solution through the flow cell 104.

By withdrawing the analyte only into a holding coil 308, 310 and not through the pumps 302, 304, the system may avoid contamination of the pump with a molecule or biomolecule that could invalidate subsequent test results. According to an embodiment, the pumps 302, 304 may comprise syringe pumps. According to another embodiment, the pumps 302, 304 may comprise flow-through pumps such as gear pumps or peristaltic pumps. When the pumps 302, 304 are flow-through pumps, they may include additional couplings (not shown) to one of the fluid sources 312, 314 or another fluid source (not shown). For example, a second set of couplings may be made to one or both of the pumps 302, 302 from the second fluid source 314 such that the pumps are primed by buffer solution. In such a case, the buffer solution may be pumped continuously or during a given pump actuation through the holding coils 308, 310. Also in such a case, the tag-team buffer solution delivery described above may be omitted, because a single pump may deliver buffer solution long enough to complete the dissociation phase.

Because the index of refraction in the flow cell 104 may be changed by pressure variations or pulsations from the pumps 302, 304, it may be desirable to use pumps that exhibit minimal pulsation. For example, one or both of the pumps 302, 304 may include a cam-driven multi-piston pump configured for minimum pressure pulsation. One example of such a pump is a MILLIGAT pump with integrated controller, model number MG1-MD, available from GLOBAL FIA.

Figure 4:
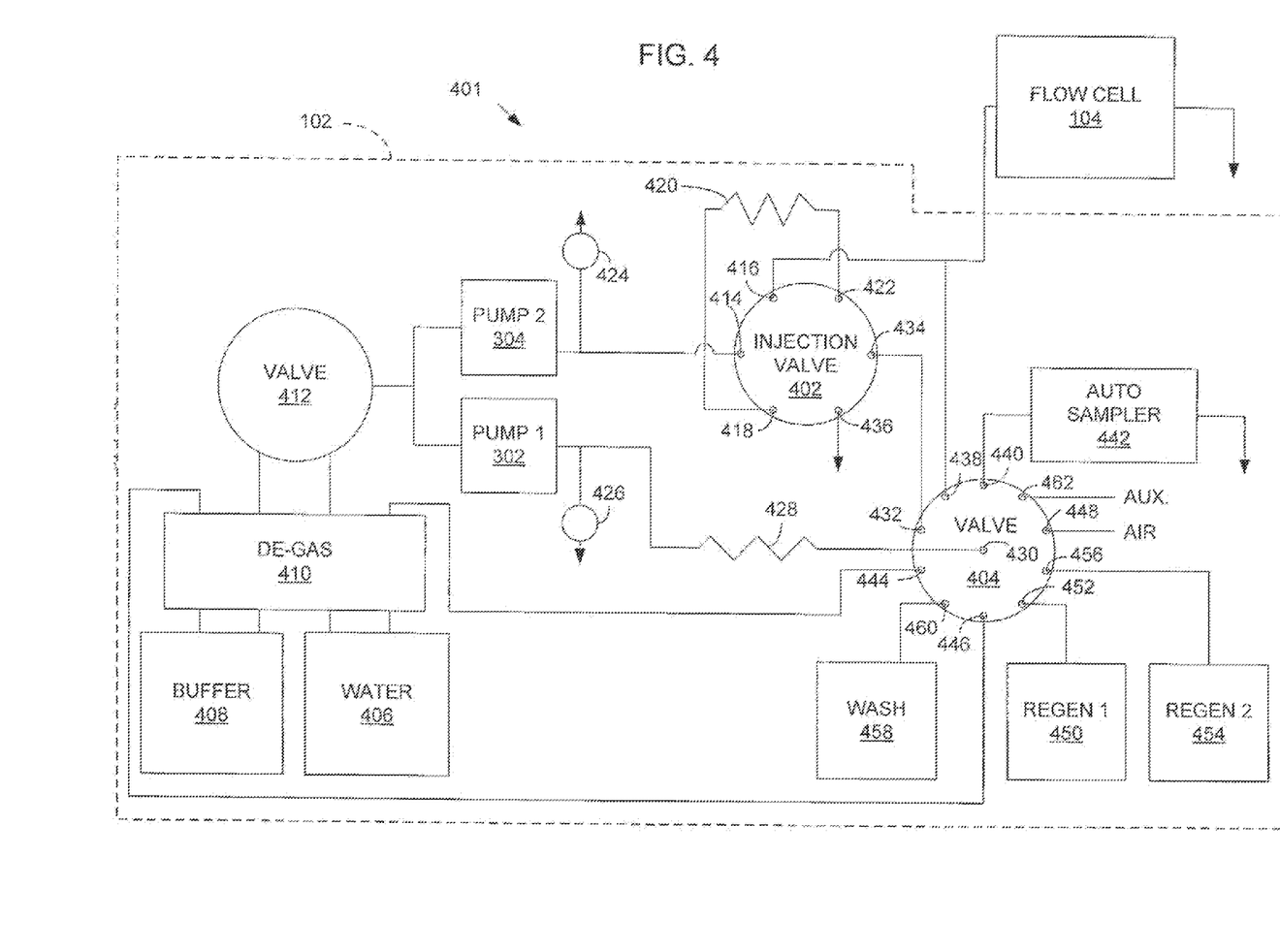
FIG. 4 is a diagram of an SPR fluid delivery system and SPR flow cell, according to another embodiment.

FIG. 4 is a diagram of an SPR fluid delivery system 102 and flow cell 104, according to another embodiment 401. The SPR fluid delivery system 102 includes first and second pumps 302, 304 configured to pump a variety of fluids through the flow cell 104 via an injection valve 402. The first and second pumps 302, 304 may each be a bidirectional fluidics pump such as a MILLIGAT pump with integrated controller, model number MG1-MD, available from GLOBAL FIA. The injection valve 402 may be a two position, six port injection valve as shown, such as a two position valve with micro electric actuators and RS-485 port, model C22-3186EHX, available from GLOBAL FIA. At least some of the fluids may be delivered to the injection valve 402 via a fluid selection valve 404, interconnected as shown. The fluid selection valve 404 may, for example, be a ten port valve selection valve such as a ten port valve with micro electric actuator and RS-485 port, model number C25Z-3180EMHX, available from GLOBAL FIA.

In forward pumping mode, the first and second pumps 302, 304 may draw fluids from a water reservoir 406 or a buffer reservoir 408, through a de-gassifier 410, according to a selected position of a three-port two-way valve 412. The three-port two-way valve 412 may be a 3-way PPS valve, 24 VDC, model number 075T3MP24-32-4, available from BIO-CHEM VALVES, for example. The de-gassifier 410 may be a mini degassing model, available from SYSTEC OEM.

The second pump 304 is coupled to a port 414 on the injection valve 402. Depending on the position of the injection valve 402, the fluid (buffer or water) pumped through port 414 may be pumped out port 416 and through the flow cell 104, or may be pumped out port 418, through a sample injection coil 420, into port 422, and out port 416 and through the flow cell. The tubing between the second pump 304 and the injection valve 402 (and thus substantially all components downstream from the second pump 304) may be protected by a pressure relief valve 424, which may for example include a 100 psi pressure relief valve, model number PRV-100, available from GLOBAL FIA. The outflow port on the pressure relief valve 424 may be coupled to a waste collection reservoir (not shown). A similar pressure relief valve 426 may be configured to protect the (forward direction) outflow port of the first pump 302.

In forward pumping mode, the first pump 302 pumps the selected fluid (water or buffer) through a holding coil 428, with the fluid in the holding coil (which may be the same or different from the fluid flowing through the first pump 302, as will be explained below) being pushed into a port 430 of the fluid selection valve 404, as shown. The holding coil 428 may, for example, include a 2 milliliter holding coil, model number CM-2000, available from GLOBAL FIA. Depending on the position of the fluid selection valve 404, the fluid may then flow out port 432 of the fluid selection valve 402 and into port 434 of the injection valve 402. Depending on the position of the injection valve, 402, the fluid may flow out port 436 to a waste reservoir (not shown). Alternatively, the fluid may flow from port 434 to port 422, and into the sample injection coil 420; and the fluid in the sample injection coil 420 then flows into port 418 and out port 436 to the waste reservoir (not shown). Alternatively, the valve 404 may be positioned such that fluid flowing from the holding coil 428 and into the input port 430 then flows out port 438 and through the flow cell 104. Such a flow path may be especially useful during priming and regeneration operational cycles described briefly above, and in more detail below. Alternatively, the valve 404 may be positioned such that fluid flowing from the holding coil 428 and into the input port 430 then flows out port 440 and into the auto sampler 442. Such a flow path may be especially useful during sampling needle flushing, wherein the fluid is flushed through the auto sampler 442 and into a waste reservoir (not shown).

The first pump 302 may also be operated in reverse pumping mode, in which case a fluid from the fluid selection valve 404 is withdrawn through port 430 and into the holding coil 428. One or more fluids from several sources may thus be loaded into the holding coil 428 for subsequent pumping through the injection valve 402 and/or the flow cell 104. The fluid selection valve may, for example be coupled to the water reservoir 406 (optionally through the degassing apparatus 410) through port 444, and to the buffer reservoir 408 (optionally through the degassing apparatus 410) through port 446. Air may be provided to the fluid selection valve, and thus to the holding coil 428, through port 448. Air may be used, for example, as bubbles to separate sequences of fluids loaded into the holding coil 428 and/or the sample injection coil 420. Such an arrangement may be particularly useful to prevent cross-contamination of fluids. A first regeneration fluid reservoir 450 may be coupled to the fluid selection valve 404 via port 452, and a second regeneration fluid reservoir 454 may be coupled to the fluid selection valve 404 via the port 456 as shown. The first regeneration fluid may for example include a detergent solution, and the second regeneration fluid may for example include an acid; either or both of which may be used, for example, to regenerate the microarray coupled to the flow cell 104. A wash reservoir 458 may be coupled to the fluid selection valve 404 via port 460, as shown. An auxiliary port 462 may be provided to couple to a second auto sampler (not shown), additional gases, other analyte sources, user-supplied fluid sources, another selection valve, and/or other fluid sources or sinks (not shown).

Figure 5:
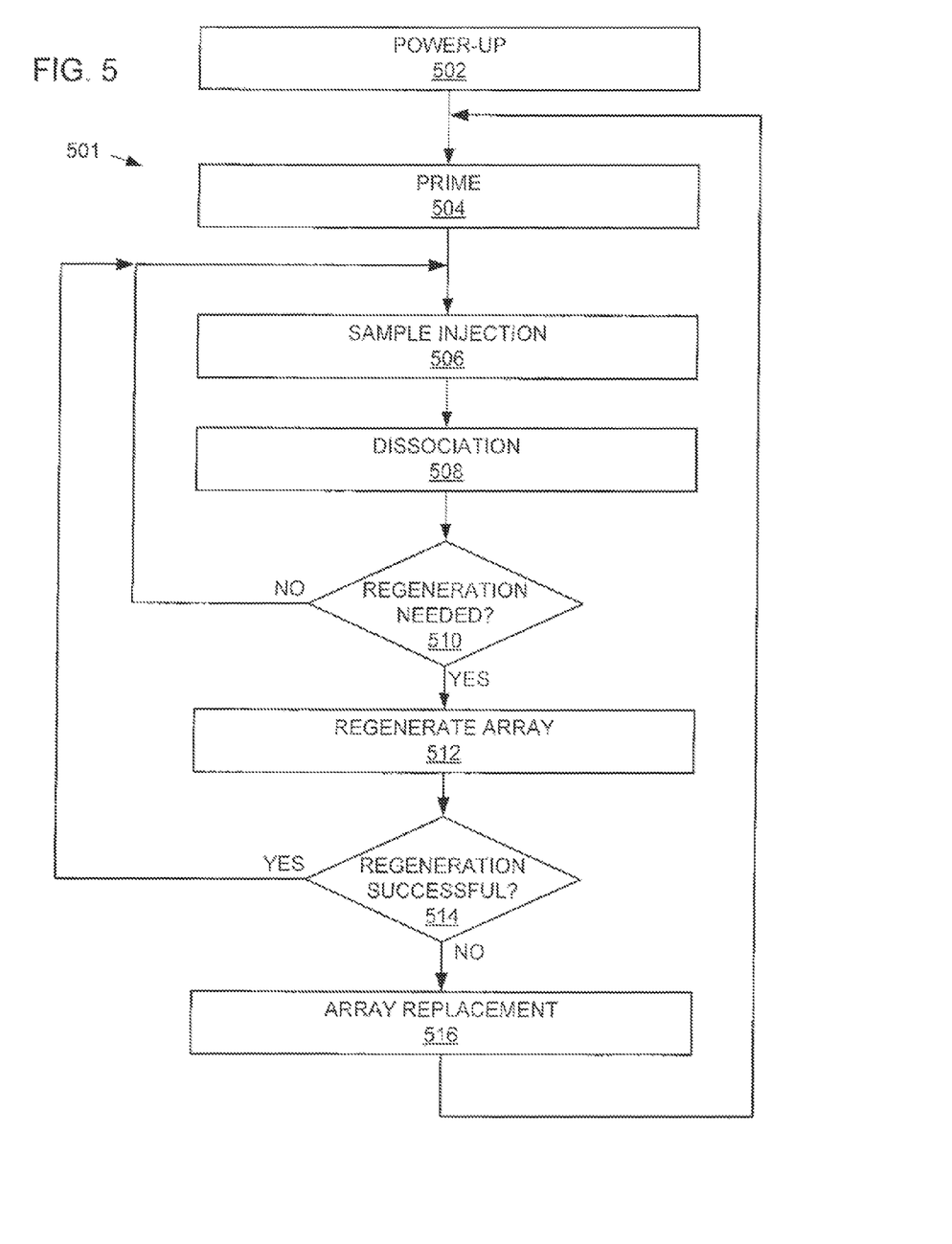
FIG. 5 is a flow chart illustrating a method for using an SPR test apparatus including an SPR fluid delivery system, such as the systems of FIG. 1, 3 or 4, according to an embodiment.

FIG. 5 is a flow chart illustrating a method 501 for using an SPR apparatus, such as the apparatus of FIG. 1, and an SPR fluid delivery system, such as the systems of FIG. 3 or FIG. 4, according to an embodiment. In step 502 the system is powered up. Numerous system checks may be made during step 502 to determine if any changes have been made to the hardware configuration, update software, etc.

Figure 6:
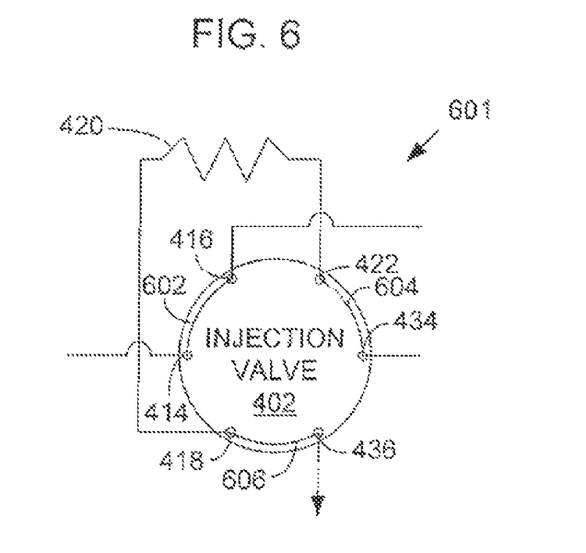
FIG. 6 is a diagram of a first position of the injection valve shown in FIG. 4 with coupling between three pairs of ports, according to an embodiment.

Proceeding to step 504, the fluidics system is primed. In step 504, the injection valve 402 may be switched to the position 601 shown in FIG. 6. Referring to FIG. 6, the first position 601 of the injection valve 402 provides a first fluid flow path 602 between port 414 (coupled to the second pump 304) and port 416 (coupled to the flow cell 104), a second fluid flow path 604 between port 434 (coupled to the selector valve 404, port 432) and port 422 (coupled to the sample injection coil), and a third fluid flow path 606 between port 418 (coupled to the other end of the sample injection coil) and port 436 (coupled to the waste outflow). The fluid selection valve 404 may be switched to couple port 430 to port 432. The valve 412 is switched to couple the buffer 408 into the pumps 302 and 304.

Pumps 1 and 2, 302, 304 pump in the forward direction. The second pump 304 fills the line to port 414 of the sample injection valve, fills the first fluid flow path 602, and fills the line exiting at port 416 and the flow cell 104 with buffer solution. The second pump may pump until the flow surfaces are fully wetted and any bubbles in the path have been cleared through the flow cell 104 and out into the waste line to the waste reservoir (not shown). Simultaneously, the first pump 302 may pump buffer solution forward to fill the holding coil 428, a fluid flow channel between port 430 and port 432 of the fluid selection valve 404, the line from port 432 to port 434 of the injection valve 402, the flow channel 604 to port 422, the sample injection coil 420, and the flow channel 606. In a manner similar to the second pump 304, the first pump 302 may continue pumping until the flow surfaces are fully wetted and any bubbles in the path have been cleared through the sample injection coil 420 and into the waste reservoir (not shown). Optionally, the second pump 304 may stop pumping before all bubbles are necessarily cleared from the flow cell 104, the first pump may briefly stop, the fluid selection valve may switch to couple port 430 to port 438, and the first pump may continue pumping to prime the line from port 438 of the fluid selection valve 404 through the line to the flow cell 104 and out into the waste reservoir (not shown). Optionally, the first pump 302 may briefly stop pumping before all the bubbles are necessarily cleared from the flow cell 104, the fluid selector valve 404 may switch to couple port 430 to port 440, and the first pump may resume pumping in the forward direction to prime the autosampler 442 and the autosampler needle (not shown) through to the waste reservoir (not shown). Optionally, the first pump 302 may briefly stop, the fluid selector valve may switch to couple port 430 to port 444, and the first pump 302 may pump in reverse to wet the surfaces and remove bubbles from the line from the buffer reservoir 408, through the degasser 410, and to port 444 of the fluid selector valve 404, withdrawing the reverse pumped fluid into the holding coil 428. Then, before any bubbles reach the first pump 302, the pump 302 may briefly stop, the fluid selection valve 404 may switch to couple port 430 to port 432, the injection valve may switch to a second position 701 shown in FIG. 7, and pump 302 may pump forward to expel bubbles from the holding coil 428 through valves 404 and 402 to the waste line coupled to port 436 of the injection valve 402.

Figure 7:
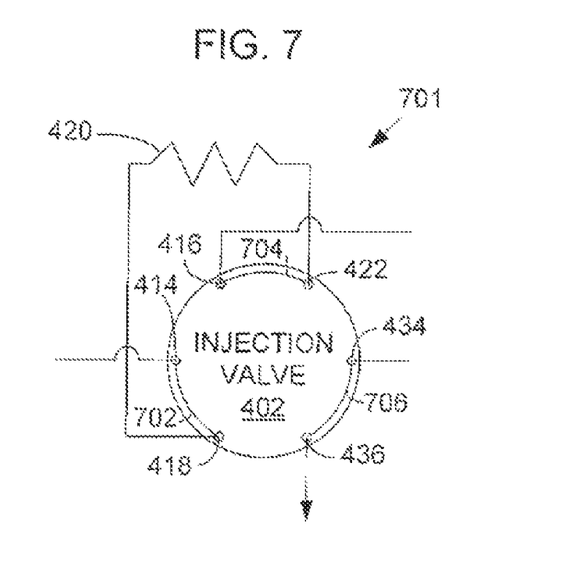
FIG. 7 is a diagram of a second position of the injection valve shown in FIG. 4 with coupling between different pairings of ports, according to an embodiment.

Referring to FIG. 7, a second position 701 of the injection valve 402 provides a first fluid flow path 702 between port 414 (coupled to the second pump 304) and port 418 (coupled to the sample injection coil), a second fluid flow path 704 between port 422 (coupled to the other end of the sample injection coil) and port 416 (coupled to the flow cell 104), and a third fluid flow path 706 between port 434 (coupled to the selector valve 404, port 432) and port 436 (coupled to the waste outflow).

Referring again to FIG. 5, step 504 and the fluid delivery system 102 shown in FIG. 4, pumps 302 and 304 and valves 402 and 404 may iteratively pump and switch port couplings to fill lines and expel bubbles as required. Typically the prime step 504 may last one to a few minutes. Following priming, the system may rest in a ready state for up to several hours without proceeding with any additional steps. The controller 116, the external computing system of network 118 of FIG. 1, or user input at a control panel may optionally initiate and repeat all or portions of the priming step 504 at intervals and/or responsive to environmental changes or other actions that may indicate the necessity of re-priming all or portions of the fluidic system 102 and/or flow cell 104.

Not shown in FIG. 5, is a "deep clean" procedure. In the deep clean procedure the pumps and valves may operate in a manner substantially similar to that described above for the prime procedure 504, except that a wash solution may be withdrawn from the wash reservoir 458 and the solution iteratively pumped through all or some of the lines and valves of the fluidics system 102 and/or flow cell 104. Such a deep clean procedure may be performed automatically or manually at intervals such as each week, each month, each 100 association tests, etc. The wash solution may include a detergent and/or a 2% hydrochloric acid solution, followed by water, followed by a solvent such as isopropyl alcohol, followed by a water rinse. The wash procedure may also involve temporary replacement of a reservoir such as the water reservoir 406 with a solvent reservoir, for example.

Returning to FIG. 5, the process 501 proceeds from the prime step 504 to the sample injection step 506. While the actions described below are referenced as occurring in a given step, it is contemplated that some of the actions extend into other steps. During (especially for the first sample run) or prior to the sample injection step 506 (especially for subsequent sample runs), the injection coil 420 is loaded (at least partially filled) with an analyte. During test runs subsequent to the first run, loading analyte into the sample injection coil as described below, may typically occur during the dissociation step 508 in preparation for looping back to the next sample injection step 506.

Referring to FIG. 4, the auto sampler 442 may for example include a 96-well auto sampling system configured to withdraw small amounts of analytes from sample wells through a robotically-operated needle. One type of relatively common laboratory automatic sampling system uses an array, such as an 8×12 array of 96 sample wells.

For a given test run, the analyte may be loaded into the sample injection coil 420 by aligning the fluid selection valve 404 to couple port 430 to port 440 and running the first pump 302 in reverse to withdraw the analyte from the auto sampler 442 into the holding coil 428. Then the fluid selection valve 404 may optionally be aligned to couple port 430 to port 446 and the first pump 302 run in reverse, withdrawing a small amount of buffer solution from the buffer reservoir 408 to clear the fluid selection valve 404. Then the fluid selection valve 404 may be aligned to couple port 430 to port 432 and the injection valve 402 may be placed in the position 601 shown in FIG. 6. Next, the first pump 302 may be run in the forward direction to push the analyte from the holding coil 428 and into the sample injection coil 420. Once the analyte is loaded in the sample injection coil 420, the sample injection to the flow cell 104 may begin.

Optionally, the fluid selection valve may align to the air port 448 before and/or after alignment to the analyte port 440, and an air bubble may be withdrawn into the holding coil 428 at the front and/or end of the analyte. The leading and trailing air bubble may then be transferred to the sample injection coil 420, along with the analyte as describe above. The presence of air bubbles at the beginning and/or end of the analyte volume may help to isolate the contents of the analyte from the leading and/or trailing buffer volume.

For embodiments where air bubbles are loaded at the edges of the analyte, one or more optional optical sensors (not shown) may be configured to sense the bubble positions and may thus be used as feedback control to determine the occurrence of fluid flow events. For embodiments not using air bubbles, the controlled volumetric flow rates of the pumps 302, 304 is typically precise enough to know fluid front locations in the system as a function of time.

At the beginning of injection of the sample, the injection valve 402 may be aligned to the position 701 shown in FIG. 7. The second pump 304 pumps in the forward direction, pushing buffer solution from port 414 to port 418 of the injection valve 402 and into the sample injection coil 420. The buffer may travel in plug flow and push the analyte in the sample injection coil through port 422 and port 416 of the injection valve, and through the flow cell 104. An association curve 202 for one or more test patches on the microarray 106 may be derived from image data produced by the detector 114.

During the injection of the sample, the first pump 302 may flush any remnants of the first analyte from the structure 102 of FIG. 4 by interactively withdrawing the remaining analyte and flushing the lines with clean buffer solution out through the waste port 436 of the injection valve and/or the waste line of the auto sampler 442.

At the end of the sample injection phase 506, the process 501 proceeds to step 508, and the dissociation phase begins. At the juncture between the phases, the injection valve 402 may quickly switch from the position 701 of FIG. 7 to the position 601 of FIG. 6. According to one embodiment, the switching time may be from about 10 milliseconds to about 100 milliseconds. According to an embodiment, the switching time may be from about a millisecond to about 10 milliseconds. According to some embodiments, the switching time may be about a millisecond or less. The second pump 304 may momentarily stop during the switch and then restart pumping in the forward direction. The second pump pushes buffer solution into port 414 of the injection valve 402, through the channel 602, and out port 416 and through the flow cell 104. Since the switching time of the injection valve 402 may be so short, localized pooling and extraneous association or entanglement of chemical and/or biochemical moieties in the analyte with the test patches may be avoided, thus providing more precise test results.

While the buffer is pumped through the flow cell 104 during the dissociation phase, the chemical and/or biochemical moieties present in the previous analyte may dissociate from the test patches on the microarray and be carried away by the moving buffer solution. A dissociation curve 204 may be derived from image measurements performed by the detector 114 and calculations performed by the controller 116 and/or the external computing system or network 118.

While the buffer is pumped through the flow cell 104 during the dissociation step 508, the first pump may load the sample injection coil 420 with another volume of the same analyte or with a next analyte from the auto sampler 442, according to the procedure described above. Thus, the procedure may loop back to step 506 as shown, allowing substantially uninterrupted sample injection 506 (association) and dissociation 508 phases.

Optionally, the process may include an automatic or semiautomatic regeneration determination step 510. As shown in FIG. 2, the ending apparent molecule or biomolecule loading 216 at the end of a dissociation phase may be somewhat higher than the beginning molecule or biomolecule loading 208. Such a change may be due, in part, to degradation of the test patch itself, non-specific molecule or biomolecule binding, and/or non-dissociated remnants of a molecules or biomolecules clinging to the test patch. Some increase in apparent loading may be tolerable and the process of repeating steps 506 and 508 may continue with the value 216 simply replacing the value 208 as the starting value for a subsequent test. In some cases, however, such degradation may interfere with measurements, shorten microarray life, etc. and it may be desirable to regenerate the microarray surface.

A determination in step 510 of whether regeneration is needed may be made, for example, by comparing successive values of the apparent loading of molecules or biomolecules and/or comparing longer term trends in apparent molecule or biomolecule loading, such as by building a series of maps of the surface of the microarray with the reflectance values or apparent loadings. Such historical maps may then be compared to a recent map (e.g. the current map or perhaps the preceding map). An algorithm or look-up-table (LUT) may then be used to determine an indication of a need to regenerate the microarray. If regeneration is not needed, the program may loop back to the sample injection step. If regeneration is indicated, the procedure may proceed to step 512, where the microarray surface is regenerated.

As indicated above, a mild detergent (e.g. REGEN 1 450) and/or a mild acid (e.g. REGEN 2 454), in combination with water rinsing may be performed to regenerate the microarray to or substantially to a previous state. The apparatus 102 of FIGS. 3 and/or 4 may operate in a manner akin to that described above to deliver regeneration fluids 450, 454 to the microarray coupled to the flow cell 104. Specifically, the regeneration fluids and water are typically delivered from the holding coil 428 through port 438 of the fluid selection valve to the flow cell. Such a flow path may allow a loaded analyte in the sample injection coil 420 to be at the ready for a subsequent sample injection step 506. Typically, the fluid lines and the flow cell 104 are refilled with buffer solution prior to resuming a sample injection step.

After attempting to return the microarray to a previous state, the image may then be analyzed again and, if need be, regeneration repeated within step 512 until either a maximum number of repeated cycles is met or the microarray is regenerated. Proceeding to step 514, if the regeneration was successful, the process may return to step 506 where the analyte held in the sample injection coil 420 is injected through the flow cell as described above. If the regeneration was unsuccessful, the process may proceed to step 516 where the microarray may be replaced with a replacement microarray. For example, a user may be alerted to manually replace the microarray. According to an embodiment, the flow cell may be evacuated (with buffer or water being replaced by air). When the replacement microarray is loaded onto the flow cell and aligned to the coupler 112 (or alternatively, when an indication is received that the user has replaced the microarray), the process may loop back to the prime step 504 where the process repeats itself.

FIG. 6 is a diagram 601 of a first position of the injection valve 402 shown in FIG. 4, according to an embodiment. The valve position 601 couples three pairs of ports. Port 414 is coupled via a flow channel 602 to port 416, port 422 is coupled via a flow channel 604 to port 434, and port 418 is coupled via a flow channel 606 to port 436. In the position 601, a fluid pushed by the first pump 302 through the selection valve 404 may arrive at port 434 and flow out port 422 into the holding coil 420. For example, the fluid may include an analyte. Fluid already in the holding coil 420 may similarly be pushed through port 418 and then flow through flow channel 606 and out port 436 to a waste receptacle.

Similarly, fluid from pump 2 304 may be pushed in port 414, flow through flow channel 602 to port 416, and then flow out through the flow cell. Pumping by pump 2 304 through flow channel 602 may occur simultaneously with pumping through flow channels 604 and 606 by pump 1 302. While the injection valve 402 is in position 601, pump 2 304 may pump buffer solution through the flow cell substantially continuously to provide for molecule or biomolecule dissociation from test patches in the flow cell. Previously loaded test patches may thus dissociate according to curve portion 204 of FIG. 2. Simultaneously, pump 1 302 may push the next analyte to be tested, such as from the autosampler 442, from the selector valve 404 and into the holding coil 420.

As indicated above, the inner surfaces of the flow channels 602, 604, 606 and the tubing 420, etc. (as well as the flow cell itself) may be formed from a hydrophilic material and/or treated with a hydrophilic substance to reduce resistance to flow. This may allow reductions in flow channel, tubing, and/or flow cell cross-sectional areas, which may allow reduced exchange volume. Appropriate treatments include incubation in a 10% ZONYL (Dupont) solution or use of silica treated tubing.

FIG. 7 is a diagram of a second position 701 of the injection valve 402 shown in FIG. 4 with coupling between different pairings of ports, according to an embodiment. Port 414 is coupled via a flow channel 702 to port 418, port 422 is coupled via a flow channel 704 to port 416, and port 434 is coupled via a flow channel 706 to port 436. In the position 701, a fluid pushed by the first pump 302 through the selection valve 404 may arrive at port 434 and flow out port 436 to a waste receptacle. For example, the fluid may include remnants of an analyte pushed by buffer or water to flush the tubing.

In configuration 701, pump 2 304 may push a buffer solution into port 414, through flow channel 702, and into the holding coil 420. Fluid already in the holding coil 420 may be pushed through port 422, through flow channel 704 and out port 416 into the flow cell. Thus, position 701 may be used during an association phase 202 shown in FIG. 2.

Thus, the high performance SPR fluidic system 201 and the methods for using it described herein may provide high throughput, high accuracy, convenience, ease-of-use, longer microarray life, longer system life, and/or other benefits.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A method for operating a surface plasmon resonance test apparatus comprising:
    transmitting a first sequence of valve and pump control signals to a fluid delivery system coupled to a flow cell and a microarray;
    receiving a plurality of images of the microarray;
    analyzing the images of the microarray to determine if the microarray has degraded; and
    if degradation has occurred, automatically transmitting a second sequence including at least one valve control signal and at least one pump control signal to pump a regeneration fluid through the flow cell and the microarray.

2. The method for operating the surface plasmon resonance test apparatus of claim 1, further comprising:
    receiving at least one post-regeneration image of the microarray;
    analyzing the post-regeneration image of the microarray to determine if the microarray is regenerated; and
    transmitting an alert message to a user if the microarray is not regenerated.

3. The method for operating the surface plasmon resonance test apparatus of claim 1, further comprising:
    receiving at least one post-regeneration image of the microarray;
    analyzing the post-regeneration image of the microarray to determine if the microarray is regenerated; and
    if the array is not regenerated, transmitting another second sequence including the at least one valve control signal and the at least one pump control signal to pump the regeneration fluid through the flow cell and microarray.

4. The method for operating the surface plasmon resonance test apparatus of claim 1, wherein the surface plasmon resonance test apparatus includes an injection valve including a first port coupled to receive fluid pushed by a first pump and a second port coupled to receive fluid pushed by a second pump, wherein a sequence of valve and pump control signals switch the fluid delivery system between the first port and the second port.

5. The method for operating the surface plasmon resonance test apparatus of claim 4, wherein the surface plasmon resonance test apparatus includes a holding coil and a flow cell, wherein a first sequence of valve and pump control signals couple the fluid delivery system between the second pump and one or both the holding coil and the flow cell.

6. The method for operating the surface plasmon resonance test apparatus of claim 5, wherein a second sequence of valve and pump control signals couple the fluid delivery system between the second pump and the flow cell and between the first pump and the holding coil.

7. The method for operating the surface plasmon resonance test apparatus of claim 4, wherein a sequence of valve and pump control signals couple the fluid delivery system between the second pump to push fluid from the holding coil through the flow cell.

8. The method for operating the surface plasmon resonance test apparatus of claim 1, wherein the surface plasmon resonance test apparatus includes an injection valve including a first port coupled to receive fluid pushed by a first pump and a second port coupled to receive fluid pushed by a second pump, wherein a sequence of valve and pump control signals switch the fluid delivery system delivering to the holding coil via the injection valve using one or both the first pump and the second pump.

9. The method for operating the surface plasmon resonance test apparatus of claim 1, wherein the surface plasmon resonance test apparatus includes a selection valve and an injection valve including a first port coupled to receive fluid pushed by a first pump and a second port coupled to receive fluid pushed by a second pump, wherein a sequence of valve and pump control signals switch the fluid delivery system between the first pump and one or both a plurality of fluid sources and the injection valve.

10. The method for operating the surface plasmon resonance test apparatus of claim 9, wherein the plurality of fluid sources includes an auto sampler.

11. A method for operating a surface plasmon resonance test apparatus comprising:
transmitting a first sequence of valve and pump control signals to a fluid delivery system coupled to deliver a plurality of analytes sequentially through a flow cell and a microarray;
receiving a plurality of images of the microarray;
analyzing the images of the microarray to determine if the microarray has degraded; and
if degradation has occurred automatically transmitting a second sequence including at least one valve control signal and at least one pump control signal to pump a regeneration fluid through the flow cell and the microarray.

12. The method for operating the surface plasmon resonance test apparatus of claim 11, wherein the surface plasmon resonance test apparatus includes an injection valve including a first port coupled to receive fluid pushed by a first pump and a second port coupled to receive fluid pushed by a second pump, wherein a sequence of valve and pump control signals switch the fluid delivery system between the first port and the second port.

13. The method for operating the surface plasmon resonance test apparatus of claim 12, wherein the surface plasmon resonance test apparatus includes a holding coil and a flow cell, wherein the first sequence of valve and pump control signals couple the fluid delivery system between the second pump and one or both the holding coil and the flow cell.

14. The method for operating the surface plasmon resonance test apparatus of claim 13, wherein a second sequence of valve and pump control signals couple the fluid delivery system between the second pump and the flow cell and between the first pump and the holding coil.

15. The method for operating the surface plasmon resonance test apparatus of claim 12, wherein a sequence of valve and pump control signals couple the fluid delivery system between the second pump to push fluid from the holding coil through the flow cell.

16. The method for operating the surface plasmon resonance test apparatus of claim 11, wherein the surface plasmon resonance test apparatus includes an injection valve including a first port coupled to receive fluid pushed by a first pump and a second port coupled to receive fluid pushed by a second pump, wherein a sequence of valve and pump control signals switch the fluid delivery system delivering to the holding coil via the injection valve using one or both the first pump and the second pump.

17. The method for operating the surface plasmon resonance test apparatus of claim 11, wherein the surface plasmon resonance test apparatus includes a selection valve and an injection valve including a first port coupled to receive fluid pushed by a first pump and a second port coupled to receive fluid pushed by a second pump, wherein a sequence of valve and pump control signals switch the fluid delivery system between the first pump and one or both a plurality of fluid sources and the injection valve.

18. The method for operating the surface plasmon resonance test apparatus of claim 17, wherein the plurality of fluid sources includes an auto sampler.

19. The method for operating the surface plasmon resonance test apparatus of claim 11, wherein the surface plasmon resonance test apparatus includes a plurality of pumps, a holding coil, a flow cell and an injection valve including a plurality of ports coupled to receive fluid pushed by the plurality of pumps, a plurality of fluid couplings between the plurality of pumps and one or both the holding coil and the injection valve, wherein a sequence of valve and pump control signals switch the fluid delivery system between a first port and a second port such that a second analyte from the plurality of analytes does not contact a first analyte from the plurality of analytes in one or more of the injection valve, the plurality of fluid couplings and the holding cell.

* * * * *